United States Patent
Paliuras et al.

(10) Patent No.: US 6,740,684 B2
(45) Date of Patent: May 25, 2004

(54) PROCESS FOR PRODUCING A STRONG-ACID CATION EXCHANGE RESIN

(75) Inventors: Mihail Paliuras, Stade (DE); Damian M. Feord, Strasbourg (FR); Johann-Wilhelm Frey, Stade (DE)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/296,561

(22) PCT Filed: Sep. 6, 2001

(86) PCT No.: PCT/US01/28215

§ 371 (c)(1), (2), (4) Date: Feb. 21, 2003

(87) PCT Pub. No.: WO02/24335

PCT Pub. Date: Mar. 28, 2002

(65) Prior Publication Data

US 2003/0212151 A1 Nov. 13, 2003

Related U.S. Application Data

(60) Provisional application No. 60/233,679, filed on Sep. 19, 2000.

(51) Int. Cl.[7] ............................ C08F 5/20; C08C 19/00; B01J 39/00
(52) U.S. Cl. ............................. 521/31; 521/32; 521/33; 525/383; 558/254; 568/727
(58) Field of Search ............................ 558/254; 521/31, 521/32, 33; 525/383; 568/727

(56) References Cited

U.S. PATENT DOCUMENTS

| | | | |
|---|---|---|---|
| 3,394,089 A | 7/1968 | McNutt et al. | 260/2.2 |
| 3,760,066 A | 9/1973 | Gammill et al. | 260/619 |
| 4,424,283 A | 1/1984 | Faler et al. | 521/32 |
| 4,584,416 A | 4/1986 | Pressman et al. | 568/727 |
| 4,595,704 A | 6/1986 | Fazio | 521/31 |
| 4,820,740 A | 4/1989 | Li | 521/32 |
| 4,825,010 A | 4/1989 | Li | 568/724 |
| 4,918,245 A | 4/1990 | Iimuro et al. | 568/727 |
| 5,075,511 A | 12/1991 | Li | 260/619 |
| 5,212,206 A | 5/1993 | Rudolph et al. | 521/32 |
| 5,589,517 A | 12/1996 | Sugawara et al. | 521/33 |

FOREIGN PATENT DOCUMENTS

EP  0 268 318  5/1998

OTHER PUBLICATIONS

"Methoden der Organischen Chemie," Houben–Weyl, Brand IX, Schwefel–, Selen–, Te;;ur–, Verbindugen, 1955, p. 750..

Primary Examiner—Robert W. Ramsuer
Assistant Examiner—Andrea D. Small

(57) ABSTRACT

A strong-acid cation exchange resin in acid form is contacted with an alkylcarhamoyl alkylthioester in the presence of water for producing a strong-acid cation exchange resin comprising a plurality of acid groups being partially neutralized with a mercaptoalkylamine. The produced partially neutralized cation exchange resin is useful as a catalyst in a process of producing a bisphienol by reaction of a phenolic compound with a carhonyl compound.

8 Claims, No Drawings

PROCESS FOR PRODUCING A STRONG-ACID CATION EXCHANGE RESIN

This application is a 371 of PCT/US01/28215 Sep. 6, 2001, which claims benefit of provisional application No. 60/233,679, Sep. 19, 2000.

BACKGROUND OF THE INVENTION

The present invention relates to a process for producing a strong-acid cation exchange resin which comprises acid groups being partially neutralized with a mercaptoalkylamine.

Strong-acid cation exchange resins which comprise acid groups being partially neutralized with a mercaptoalkylamine and their use in the production of bisphenols is known in the art.

U.S. Pat. No. 3,394,089 describes a process for the preparation of bisphenol A from acetone and phenol in the presence of a strong-acid cation exchange resin wherein from 5 to 25 percent of the acid groups are neutralized with a $C_{1-4}$-alkyl mercaptoamine. The mercaptoalkylamine is an effective promoter for the acid catalyzed condensation of phenol and acetone. The neutralization is carried out by direct contact with the $C_{1-4}$-alkyl mercaptoamine or by exchange with its amine salt. According to the example an aqueous slurry of sulfonic acid cation-exchange resin in acid form is contacted with an aqueous solution of mercaptoethyl amine hydrochloride.

U.S. Pat. No. 5,212,206 discloses that the partially neutralized cation exchange resin as described in U.S. Pat. No. 3,394,089 is unsuitable in the bisphenol production because of the instability of the catalyst. To overcome this deficiency, U.S. Pat. No. 5,212,206 teaches that the strong acid cation-exchange resin is neutralized with a mercaptoamine in an anhydrous medium.

U.S. Pat. No. 4,584,416 discloses partial neutralization of a sulfonated ion exchange resin by means of an N-alkylamino alkyirnercaptan hydrochloride or hydrotosylate salt.

U.S. Pat. No. 5,589,517 discloses the partial neutralization of a sulfonated ion exchange resin by contacting the ion exchange resin with an N,N-dialkylmercaptoalkylamine, an N-mercaptoalkylpyrrolidine or an N-mercaptoalkylpiperidine.

U.S. Pat. No. 3,760,006 teaches that the modification of a strong-acid cation exchange resin in acid form by partial neutralization with a thiazolidine yields an improved catalyst for the preparation of bisphenol.

U.S. Pat. No. 4,595,704 discloses that known methods for producing partially neutralized ion-exchange resins employ azirine compounds which are somewhat hazardous. The U.S. patent suggests the use of less costly and less hazardous N-(2-mercaptoalkyl)amides to prepare a strong-acid cation exchange resin which is partially neutralized with an aminoalkanethiol.

U.S. Pat. No. 4,918,245 teaches that it has been known that markedly decreased amounts of Dianin's compound are produced as by-products in the bisphenol A production if an ion exchange resin is used as a catalyst of which the functional groups are modified with mercapto groups, such as by reaction with a mercaptoethylamine. On the other hand, the US patent also discloses that o,p'-isomer is still formed as a by-product in a large amount.

Unfortunately, sulfur-containing compounds which comprise a thiol group are sensitive to attack by oxygen and metals. Accordingly, the storage of these compounds without special care results in a reduced activity of strong-acid cation exchange resins which are partially neutralized with such compounds. When the partially neutralized strong-acid cation exchange resin is used as a promoter for producing bisphenol A, a variation in promoter quality may result in product variation, which is undesirable.

Accordingly, it would be desirable to find a new process for producing a strong-acid cation exchange resin comprising a plurality of acid groups being partially neutralized with a mercaptoalkylamine. It would be particularly desirable to find a process wherein the starting material used for neutralization is not sensitive to attack by oxygen and metals.

SUMMARY OF THE INVENTION

One aspect of the present invention is a process for producing a strong-acid cation exchange resin comprising a plurality of acid groups being partially neutralized with a mercaptoalkylamine, wherein a strong-acid cation exchange resin in acid form is contacted with an alkylcarbamoyl alkylthioester in the presence of water.

Another aspect of the present invention is a process of producing a bisphenol wherein a phenolic compound is reacted with a carbonyl compound in the presence of the strong-acid cation exchange resin produced according to the process above.

Yet another aspect of the present invention is a process for isomerizing by-products resulting from the production of a bisphenol by reaction of a phenolic compound with a carbonyl compound wherein the by-products are contacted with a strong-acid cation exchange resin produced according to the process above.

DETAILED DESCRIPTION OF THE INVENTION

The alkylcarbamoyl alkylthioester can be prepared by known methods, such as taught in Houben-Weyl, Volume IX, page 750, Georg Thieme editor Stuttgart, 1955. It is not sensitive to attack by oxygen and metals to a substantial degree.

Preferred alkylcarbamoyl alkylthioesters are represented by the formula I $$R^1—C(O)—NH—R^2—S—C(O)—R^3 \qquad (I)$$

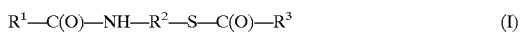

wherein $R^1$ and $R^3$ each independently is a $C_{1-4}$-alkyl group, preferably methyl, ethyl or propyl; and $R^2$ is a $C_{2-6}$-alkylene group.

More preferably, $R^1$ and/or $R^3$ is methyl. Most preferably, both groups $R^1$ and $R^3$ are methyl.

Useful $C_{2-6}$-alkylene groups are ethylene, n-propylene, isopropylene, n-butylene, isobutylene, n-pentylene, isopentylene, neopentylene, n-hexylene and all hexylene isomers. The most preferred $C_{2-6}$-alkylene group is n-propylene.

Preferred alkylcarbamoyl alkylthioesters are thioacetylalkyl amides. More preferred are thioacetylalkyl acetamides, such as thioacetylethyl acetamide, thioacetyl-n-propyl acetamide, thioacetyl-isopropyl acetamide, thioacetyl-n-butyl acetamide, thioacetyl-isobutyl acetamide, thioacetyl-n-pentyl acetamide, thioacetyl-isopentyl acetamide, thioacetyl-neopentyl acetamide, thioacetyl-n-hexyl acetamide or isomers thereof The most preferred alkylcarbamoyl alkylthioester is a compound of formula I wherein $R^1$ and $R^3$ each are methyl and $R^2$ is n-propylene, that means thioacetyl-n-propyl acetamide.

The process of the present invention is employed to modify a strong-acid cation exchange resin. Strong-acidic cation exchange resin are known in the Art, see for example "Ullmann's Enzyklopaedie der Technischen Chemie", 4th Edition, Vol. 13, pages 297 and following. Usually they have a polymeric matrix and functional ion exchange groups.

One known type of matrix is based on phenol/formaldehyde or benzene condensation polymers that are cross-linked with an aldehyde, a chlorinated hydrocarbon or an epoxy compound. The preferred matrixes are cross-linked polystyrene or cross-linked poly(alpha-methylstyrene) or a cross-linked polymer of styrene or alpha-methylstyrene which is substituted at the benzene ring with $C_{1-6}$-alkyl, for example methyl, ethyl, tert. butyl or isopropyl, or with halogeno-$C_{1-6}$-alkyl, such as chloromethyl, or with aminomethyl. The cross-linking agent preferably is divinylbenzene or trivinylbenzene.

The functional groups can be directly or indirectly bound to the polymeric matrix. For example the functional groups can be bound to the polymeric matrix via alkylene groups such as $C_{1-3}$-alkylene groups, preferably ethylene or methylene with methylene being the most preferred group.

Functional groups typically are —$SO_3H$ or -$PO_3HR$ groups wherein R is hydrogen, a $C_{1-6}$-alkyl group, such as a methyl, ethyl, n-propyl, isopropyl, n-butyl, isobutyl, the pentyl or hexyl groups, a $C_{3-6}$-cycloalkyl group, such as cyclohexyl, or aryl, such as phenyl or benzyl. The most preferred functional group is —$SO_3H$. A part of the functional groups can be present in the salt form, for example in the alkali or alkaline earth metal salt form. However, preferably more than 95 percent, more preferably more that 99 percent, most preferably substantially all functional groups are in the acid form prior to partial neutralization according to the process of the present invention.

Examples of suitable strong-acid cation exchange resins include perfluorinated sulfonic acid resins, strong-acid resins prepared by phosphonation of styrene-divinylbenzene resins, sulfonated phenol-formaldehyde resins, sulfonated polystyrene resins, sulfonated styrene-divinylbenzene resins and polymers such as those disclosed in U.S. Pat. Nos. 4,303,551 and 4,330,654. The sulfonated resins are commercially available as gelular and macro-reticular types. Particularly suitable are aromatic sulfonic acid resins having a cation exchange capacity of at least 0.5 meq/g dry weight and advantageously 2.0 meq/g. Commercial strong-acid cation exchange resins prepared by the sulfonation of a styrene-divinylbenzene resin, as described, for example, in U.S. Pat. Nos. 2,597,438; 2,642,417 or 3,037,052 are most preferably used. Such commercial sulfonic acid resins are Dowex 50 resins, Amberlite IR-120 resin, Amberlite 200 resin and Duolite C20 resin which normally have an exchange capacity of from 4 to 5.5 meq/g dry weight (Dowex, Amberlite and Duolite are trademarks).

The strong-acid cation exchange resin is partially neutralized by contacting it with an alkylcarbamoyl alkylthioester in the presence of water. Typically about a molar equivalent of alkylcarbamoyl alkylthioester is employed per equivalent of hydrogen ions to be neutralized. Water is employed in an amount sufficient to hydrolyze the alkylcarbamoyl alkylthioester to the corresponding mercaptoalkylamine. Without wanting to be bound to a theory, it is believed that the hydrolyzation of the alkylcarbamoyl alkylthioester to the corresponding mercaptoalkylamine and the partial neutralization of the acid groups of the cation exchange resin occur simultaneously. The hydrolysis is substantially quantitative. Typically from 0.2 to 5, preferably from 0.5 to 3, volumes of water are employed per volume of resins beads. Water can be used alone or in combination with an organic solvent. Preferred organic solvents are ketones, such as acetone, alcohols, such as methanol or ethanol, phenols, such as phenol, or aromatic hydrocarbons, such as toluene. The partial neutralization of the catalyst with the alkylcarbamoyl alkylthioester is preferably carried out at a temperature of from 50 to 120° C., more preferably from 80 to 110° C., most preferably at reflux temperature. The extent of neutralization of the catalyst may vary widely. Typically from 5 to 60 mole percent, preferably from 10 to 40 mole percent, more preferably from 15 to 35 mole percent of the acidic groups of the cation exchange resin are neutralized. The degree of neutralization is readily verified by measuring via conventional methods, such as titration using NaOH, the ion exchange capacity of the resin before and after neutralization.

The produced partially neutralized strong-acid cation exchange resin is an effective catalyst for the preparation of many bisphenols by reaction of a phenolic compound with a carbonyl compound.

The reaction of a phenolic compound with a stoichiometric excess of a carbonyl compound is known in the art. The process is described in general in U.S. Pat. Nos. 3,049,569 and 4,107,218 and in the references cited therein. The molar ratio between the phenolic compound and the carbonyl compound preferably is between 2:1 and 45:1, more preferably from 4:1 to 14:1.

Useful phenolic compounds should be unsubstituted in para position, but they can be substituted in ortho- or meta-position with one or more non-reactive groups, such as alkyl or halo. Preferred phenolic compounds are those of formula (II)

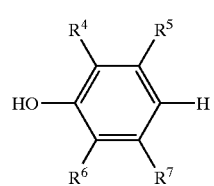

(II)

wherein $R^4$, $R^5$, $R^6$ and $R^7$ independently of one another represent hydrogen, halogen, preferably chlorine or bromine, or $C_{1-8}$-alkyl, preferably methyl, ethyl or tertiary butyl.

Preferred examples of the compounds of formula (II) are phenol, mono-, di-, tri- or tetraalkylphenols, such as o-cresol or m-cresol; o-sec.butylphenol, o-tert.butylphenol, 2,6-dimethylphenol, 3,5-dimethylphenol, 2-methyl-6-tert.butylphenol, 2-isopropyl-5-methyl-phenol, 5-isopropyl-2-methyl-phenol, 2-methyl-6-ethylphenol, 2,3,6-trimethylphenol, 2,3,5,6-tetramethylphenol, 2,6-ditertiary-butylphenol, 3,5-diethylphenol or 2-methyl-3,5-diethylphenol; chlorophenols, such as o-chlorophenol or m-chlorophenol; dichlorophenols or bromophenols, such as o-bromophenol.

The carbonyl compound employed for producing the bisphenol can be a ketone or an aldehyde. Preferred carbonyl compounds are those of the following formula III

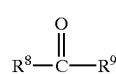

(III wherein
  $R^8$ is an aliphatic, cycloaliphatic, aromatic or heterocyclic group, and $R^9$ is hydrogen or an aliphatic, cycloaliphatic, aromatic or heterocyclic group or $R^8$ and $R^9$ together represent a divalent aliphatic or aromatic group.

Preferred groups $R^8$ and $R^9$ are $C_{1-8}$-alkyl, $C_{5-6}$-cycloalkyl, $C_{5-10}$-aryl, preferably phenyl, or $C_{7-12}$-aralkyl, preferably phenyl-$C_{1-4}$-alkyl, more preferably benzyl. These groups are optionally halogenated. When $R^8$ and $R^9$ together represent a divalent aliphatic group, the group preferably is —($R^{10}$ $CR^{11})_n$— wherein $R^{10}$ and $R^{11}$ in each occurrence individually selectable are hydrogen or $C_{1-6}$-alkyl, such as methyl or ethyl, and n is an integer from 4 to 7, preferably 4 or 5.

Examples of suitable ketones include, for example, acetone, 1,3-dichloroacetone, methyl ethyl ketone, diethyl ketone, dibutyl ketone, methyl isobutyl ketone, cyclohexanone, fluorenone, preferably 9-fluorenone, propionylphenone, methyl amyl ketone, mesityl oxide, cyclopentanone or acetophenone. Examples of suitable aldehydes include formaldehyde, acetaldehyde, propionaldehyde, butyraldehyde and benzaldehyde. The most preferred carbonyl compound is acetone.

The phenolic compound and the carbonyl compound are preferably reacted at a temperature of from 35 to 100° C., more preferably from 40 to 90° C., most preferably from 45 to 85 ° C.

The strong-acid cation exchange resin modified according to the present invention is particularly useful in the production of bisphenol A from phenol and acetone. It has been surprisingly found that a higher purity of the 4,4'-dihydroxy-2,2-diphenylpropane (commonly called the p,p'-isomer of bisphenol A or simply bisphenol A) can be achieved when using the strong-acid cation exchange resin modified according to the present invention as a catalyst instead of a strong-acid cation exchange resin which has been modified with dimethylthiazolidine or cysteamine hydrochloride, both of which are commonly used modifiers. When using the strong-acid cation exchange resin modified according to the present invention, the amount of the undesired by-product 2,4'-dihydroxy-2,2-diphenylpropane (commonly called the o,p'-isomer of bisphenol A) is generally only up to about 2 percent, based on the weight of the p,p'-isomer of bisphenol A. This amount is generally at least about 15 percent lower, in many cases even at least about 20 percent lower than the amount of the o,p'-isomer of bisphenol A that is obtained in the presence of a corresponding strong-acid cation exchange resin which has been modified with dimethylthiazolidine or cysteamine hydrochloride.

Furthermore, the strong-acid cation exchange resin produced according to the present invention is useful as a catalyst for isomerizing by-products resulting from the above-described production of a bisphenol, preferably for isomerizing by-products which result from the production of bisphenol A and which include 2,4'-dihydroxy-2,2-diphenylpropane. The produced strong-acid cation exchange resin is particularly useful for isomerizing 2,4'-dihydroxy-2,2-diphenylpropane to 4,4'-dihydroxy-2,2-diphenylpropane. The isomerization process is generally known in the art.

The following examples are provided to illustrate the present invention. The examples are not intended to limit the scope of the present invention and they should not be so interpreted. Amounts are in weight parts or weight percentages unless otherwise indicated.

EXAMPLE 1

Preparation of Thioacetylpropyl Acetamide 58 g of thioacetic acid are placed in a flask. 350 g of a 15 percent solution of sodium ethoxide in ethanol is added drop by drop under cooling by nitrogen and ice. Afterwards 320 g of a 12.4 percent solution of 3-chloropropylamine hydrochloride in ethanol are added to the above solution. The mixture is heated under reflux for 1 hour, cooled to room temperature and filtrated. The ethanol is evaporated and the residue is dissolved in acetone to precipitate any residual sodium chloride. After filtration the acetone is removed. Thioacetylpropyl acetamide remains as viscous oil.

Preparation of the Partially Neutralized Cation Exchange Resin 30 g of thioacetylpropyl acetamide produced above, 500 ml of a wet, strong-acid cation exchange resin which comprises sulfonic acid groups and a polymer matrix of styrene cross-linked with 4 percent of divinylbenzene, 1000 ml of water and 50 ml of methanol are placed in a flask. The strong-acid cation exchange resin is commercially available under the trademark DOWEX 50WX4 from The Dow Chemical Company and has a cation exchange capacity of 1.2 meg/ml (5.3 meq/g). The mixture is stirred under reflux for 6 hours and then cooled to room temperature. The resin is filtrated and washed with acetone and water. Analysis of the resin by titration with NaOH shows that 23 percent of its acid capacity is neutralized with 3-mercaptopropylamine.

Comparative Example A 4 g of 2,2-dimethylthiazolidine, 100 ml of the above-described strong-acid cation exchange resin, which is commercially available under the trademark DOWEX 50WX4 from The Dow Chemical Company, and 250 ml of water are stirred for one hour at room temperature, then filtrated and washed with another 250 ml of water.

A cation exchange resin is prepared of which 25 percent of its acid capacity is neutralized with 2,2-dimethylthiazolidine.

Comparative Example B 4 g of 2-mercaptoethylamine hydrochloride (also designated as cysteamine hydrochloride), 100 ml of the above-described strong-acid cation exchange resin, which is commercially available under the trademark DOWEX 50WX4 from The Dow Chemical Company, and 250 ml of water are stirred for one hour at room temperature, then filtrated and washed with another 250 ml of water.

A cation exchange resin is prepared of which 25 percent of its acid capacity is neutralized with 2-mercaptoethylamine.

Use of the Modified Catalyst

A stainless steel reactor column is charged with 500 ml of the partially neutralized cation exchange resin prepared according to Example 1 or Comparative Example A or B. The resin is dried by flushing the resin bed with twice its volume of phenol at 60° C. The catalyst is ready for use. The catalyst activity is tested by pumping a liquid consisting of phenol and acetone in a molar ratio of 10:1 at a speed of 4ml/min. through the column containing the catalyst at 70° C. The amounts of bisphenol A (the p,p'-isomer) and of the o,p'-isomer of bisphenol A in the resulting product mixture are analyzed by gas chromatography. The percent o,p'-isomer, based on the weight of the p,p'-isomer of bisphenol A, is listed in Table 1 below.

TABLE 1

| (Comparative) Example | Compound used for neutralization | Percent Neutralization | Percent o,p'-isomer |
|---|---|---|---|
| 1 | Thioacetylpropyl acetamide | 23 | 1.9 |
| A | Dimethylthiazolidine | 25 | 2.5 |
| B | 2-mercaptoethylamine hydrochloride | 25 | 2.5 | percentage of o,p'-isomer, that means a purer product is obtained according to Example 1, as compared to Comparative Examples A and B. The small difference in neutralization of the acid groups (23 percent in Example 1 but 25 percent in Comparative Examples A and B) does not influence the percentage of o,p'-isomer.

What is claimed is:

1. A process for producing a strong-acid cation exchange resin comprising a plurality of acid groups being partially neutralized with a mercaptoalkylanine, wherein a strong-acid cation exchange resin in acid form is contacted with an alkylcarbamoyl alkylthioester of the formula I

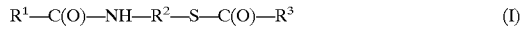

$$R^1\text{—C(O)—NH—}R^2\text{—S—C(O)—}R^3 \quad (I)$$

wherein
$R^1$ and $R^3$ are each independently a $C_{1-4}$-alkyl group, and $R^2$ is a $C_{2-6}$-alkylene group
in the presence of water.

2. The process of claim 1 wherein $R^1$ or $R^3$ or both are methyl.

3. The process of claim 2 wherein in formula I $R^1$ and $R^3$ each are methyl and $R^2$ is propylene.

4. The process according to claim 1 wherein the strong-acid cation exchange resin comprises sulfonic acid groups and has an initial cation exchange capacity of at least 0.5 meq/g dry resin in acid form.

5. The process according to claim 1 wherein the strong-acid cation exchange resin is a salfonated styrene-divinylbenzene resin.

6. The process according to claim 1 wherein from 5 to 60 mole percent of the acidic groups are neutralized.

7. A process for producing a bisphenol wherein a phenolic compound is reacted with a carbonyl compound in the presence of a strong-acid cation exchange resin produced according to the process of claim 1.

8. The process of claim 7 wherein phenol is reacted with acetone.

* * * * *